United States Patent [19]

Bloom, deceased et al.

[11] 4,311,638

[45] Jan. 19, 1982

[54] SILVER COMPLEXING AGENTS

[75] Inventors: Stanley M. Bloom, deceased, late of Waban, Mass., by Arlene N. Bloom, executrix; Krishna G. Sachdev, Beacon, N.Y.

[73] Assignee: Polaroid Corporation, Cambridge, Mass.

[21] Appl. No.: 202,295

[22] Filed: Oct. 30, 1980

Related U.S. Application Data

[62] Division of Ser. No. 80,350, Oct. 1, 1979, Pat. No. 4,267,256.

[51] Int. Cl.$^3$ .................. C07D 285/00; C07D 291/02
[52] U.S. Cl. ..................................................... 260/330
[58] Field of Search ......................................... 260/330

[56] References Cited

U.S. PATENT DOCUMENTS

| | | | |
|---|---|---|---|
| 3,062,646 | 11/1962 | Dann et al. | 96/66 |
| 3,930,867 | 1/1976 | Bigelow | 96/107 |
| 4,017,314 | 4/1977 | Blake | 96/66 R |

OTHER PUBLICATIONS

Tetrahedron Letters, Pelissard and Louis, vol. 45, pp. 4589–4592 (1972).

Inorganic Nuclear Chemistry Letters, Louis et al., vol. 13, pp. 31–35 (1977).

*Primary Examiner*—Richard Raymond
*Attorney, Agent, or Firm*—Gaetano D. Maccarone

[57] ABSTRACT

There are described photographic products, processes and compositions wherein cyclic crown ether ligands are utilized as silver halide solvents. Also disclosed are novel cyclic crown ether ligands.

9 Claims, No Drawings

SILVER COMPLEXING AGENTS

This is a division of application Ser. No. 080,350, filed Oct. 1, 1979, now U.S. Pat. No. 4,267,256.

BACKGROUND OF THE INVENTION

This application relates generally to photography and more particularly to photographic products, processes and compositions which include cyclic crown ether ligands as silver halide solvents.

Photographic processing compositions capable of forming water-soluble complex silver salts are known to be useful in many types of silver halide photography. In conventional or "tray" development, it is customary to fix the developed silver halide emulsion by applying a solution of silver halide solvent, i.e., silver halide complexing agent which forms a water-soluble silver complex with the residual silver halide. The water-soluble silver complex thus formed and excess silver halide solvent are then removed from the developed and fixed emulsion by washing with water.

Silver halide solvents also have been employed in monobaths where a single processing composition containing a silver halide developing agent in addition to the silver halide solvent is utilized for both developing and fixing an exposed photosensitive silver halide layer. Silver halide solvents also have been employed in diffusion transfer photographic processes. Such processes are now well known in the art; see for example, U.S. Pat. Nos. 2,543,181; 2,647,056; 2,983,606; etc. In processes of this type, an exposed silver halide emulsion is treated with a processing composition whereby the exposed silver halide emulsion is developed and an imagewise distribution of diffusible image-forming components is formed in the unexposed and undeveloped portions of the silver halide emulsion. This distribution of image-forming components is transferred by imbibition to an image-receiving stratum in superposed relationship with the silver halide emulsion to provide the desired transfer image. In diffusion transfer processes where a silver transfer image is formed, processing is effected in the presence of a silver halide solvent which forms a diffusible complex with the undeveloped silver halide. The soluble silver complex thus formed diffuses to the superposed image-receiving layer where the transferred silver ions are deposited as metallic silver to provide the silver transfer image. In preparing silver prints in this manner, the image-receiving element preferably includes a silver precipitating agent, for example, heavy metal sulfides and selenides as described in U.S. Pat. No. 2,698,237.

The present invention is concerned with new photographic compositions, processes and products as well as novel silver halide solvents.

SUMMARY OF THE INVENTION

It is therefore the object of this invention to provide photographic products, processes and compositions wherein cyclic crown ether ligands are utilized as silver halide solvents.

It is another object to provide novel cyclic crown ether ligands.

BRIEF SUMMARY OF THE INVENTION

These and other objects and advantages of the invention are accomplished by providing photographic products, processes and compositions which include, as silver halide solvents, at least one silver complexing compound which is represented by the structural formula

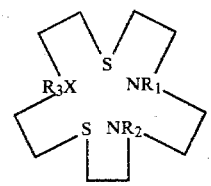

wherein X may be selected from the group consisting of oxygen, nitrogen, sulfur, phosphorous and selenium;

$R_1$ and $R_2$ may be the same or different and may be H, alkyl, hydroxyalkyl, alkoxyalkyl or aminoalkyl, preferably having from two to six carbon atoms,

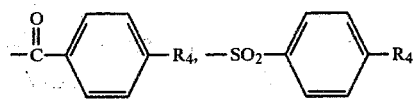

and

wherein $R_4$ may be H, alkyl, alkoxy or $-NO_2$ and $R_5$ may be H, alkyl, alkoxy or alkoxyalkyl; and when X is $-N-$, $R_3$ may be H, alkyl, hydroxyalkyl, alkoxyalkyl or aminoalkyl, preferably having from two to six carbon atoms,

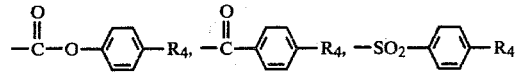

or $-CH_2-CH=CH-R_6$, wherein $R_6$ may be H, alkyl, cyano or

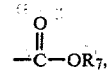

wherein $R_7$ may be H or alkyl.

The compound wherein X is oxygen and $R_1$ and $R_2$ are both hydrogen is disclosed in Tetrahedron Letters, Pelissard and Louis page 4589 (1972). The other compounds which are within the general formula are per se novel compounds.

DESCRIPTION OF THE PREFERRED EMBODIMENTS

One class of specific preferred silver complexing compounds which are suitable for use according to the invention is represented by the general formula

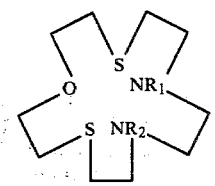

wherein $R_1$ and $R_2$ are as described in Table I

TABLE I

| Compound | $R_1$ | $R_2$ |
|---|---|---|
| A | H | H |
| B | CH₃ | CH₃ |
| C | −C(=O)−C₆H₄−NO₂ | H |
| D | −C(=O)−C₆H₄−NO₂ | −C(=O)−C₆H₄−NO₂ |
| E | −SO₂−C₆H₄−CH₃ | H |
| F | −SO₂−C₆H₄−CH₃ | −SO₂−C₆H₄−CH₃ |
| G | −C(=O)−CH₃ | −C(=O)−CH₃ |
| H | −C(=O)−CH₃ | H |

Other specific preferred silver complexing compounds which are suitable for use according to the invention are represented by the following formulas:

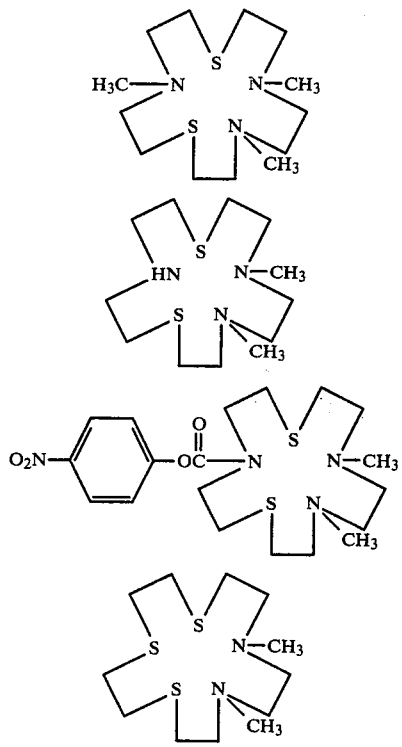

Compounds A, B, I, J and L are stable in an alkaline environment, have a melting point less than about 50° C. and the log of the stability constant ($\beta$) for a 1:1 complex of the complexing agent with silver is at least about 10.5. By "stable in an alkaline environment" is meant that the silver complexing agent retains at least 75% of its silver complexing ability after being in a 1 N sodium hydroxide solution for twenty-four hours at room temperature. These preferred complexing agents can be used in a diffusion transfer photographic method for making positive transparencies, without washing, which are substantially completely free of crystals. The method is described and claimed in applicants' copending application Ser. No. 080,349, filed on even date herewith now U.S. Pat. No. 4,267,254. Accordingly, these compounds are the preferred silver complexing agents of the invention.

Compound A may be synthesized according to the method described in Tetrahedron Letters, 45, pp 4589–4592 (1972). The pentadentate macrocyclic ligands B, I, J and L can be prepared by reacting N,N'-dimethyl-N,N'bis(2-mercaptoethyl) ethylenediamine [for its preparation see J. Amer. Chem. Soc., 98, page 6951 (1976)] with (Cl CH₂CH₂)₂X (where X may be O, N-Me, NH or S) in a suspension of sodium hydride in tetrahydrofuran. Compounds such as C—H may be prepared from compound A by reaction with appropriate acyl halides. Similarly, compound K may be prepared from compound J by reaction with p-nitrophenyl chloroformate. The desired ligands can be separated from the crude reaction products by first treating their methanol solution with silver thiocyanate to form the 1:1 ligand-silver thiocyanate complex which preferentially crystallizes from solution while the impurities remain in the filtrate. Recrystallization of the complex followed by precipitation of silver as silver sulfide with hydrogen sulfide and liberation of the free ligand by passing an aqueous solution of the resulting thiocyanic acid complex through an anion exchange column provides essentially pure samples of the ligands. Alternatively purification can be effected by chromatography of the crude product mixture on silica gel, a more time consuming procedure.

As mentioned previously, the compounds represented by the general formula are useful as silver complexing agents in photography. The log of the stability constant ($\beta$) for the 1:1 complex of various preferred compounds is shown in Table II. The stability constants were determined by potentiometry, i.e., by titrating the ligand with a standardized solution of silver perchlorate in mildly alkaline, constant pH, constant ionic strength medium (0.05 M NaOH, 0.10 M NaClO₄). All solutions and titrants were prepared carbonate free and with an ionic strength of 0.1 (NaClO₄) except when the perchlorate salt of the complex was found to be insoluble. In those cases perchlorate was omitted from the system. An argon atmosphere was used throughout. The indicating electrode was a silver specific ion type used in conjunction with a sleeve type double junction. Ag-/AgCl reference electrode.

TABLE II

| Compound | Log $\beta$ |
|---|---|
| A | 11.37 ± .01 |
| B | 11.84 ± .01 |
| I | 12.30 ± .01 |
| J* | 11.98 ± .02 |
| L | 11.84 ± .02 |

*No perchlorate was added

In formulating photographic processing compositions utilizing the above-described compounds, the compounds may be used singly or in admixture with each other or with other silver halide solvents. The total amount employed may vary widely depending upon the particular photographic system and should be used, for example, in a quantity sufficient for fixing a developed negative in conventional "tray" processing or in a quantity sufficient to give a satisfactory transfer print in diffusion transfer processes under the particular processing conditions employed.

Though the silver halide solvents of the present invention are broadly useful in a variety of photographic processes of the type in which water-soluble silver complexes are formed from the unreduced silver halide of a photoexposed and at least partially developed silver halide stratum, they find particular utility in diffusion transfer processes. A composition embodying the present invention specifically suitable for use in the production of transfer images comprises, in addition to the silver complexing agents of the above-described type, a suitable silver halide developing agent. Examples of developing agents that may be employed include hydroquinone and substituted hydroquinones, such as tertiary butyl hydroquinone, 2,5-dimethylhydroquinone, methoxyhydroquinone, ethoxyhydroquinone, chlorohydroquinone; pyrogallol and catechols, such as catechol, 4-phenyl catechol and tertiary butyl catechol; aminophenols, such as 2,4,6-triamino-orthocresol; 1,4-diaminobenzenes, such as p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid, and other enediols, such as tetramethyl reductic acid; and hydroxylamines, such as N,N-di-(2-ethoxyethyl)hydroxylamine and N,N-di-(2-methoxyethoxyethyl)hydroxylamine.

In diffusion transfer processes, the processing composition, if it is to be applied to the emulsion by being spread thereon in a thin layer, also usually includes a viscosity-imparting reagent. The processing composition may comprise, for example, one or more silver halide solvents of the present invention, one or more conventional developing agents such as those enumerated above, an alkali such as sodium hydroxide or potassium hydroxide and a viscosity-imparting reagent such as a high molecular weight polymer, e.g., sodium carboxymethyl cellulose or hydroxyethyl cellulose.

In one such transfer process, the processing solution is applied in a uniformly thin layer between the superposed surfaces of a photoexposed photosensitive element and an image-receiving element, for example, by advancing the elements between a pair of pressure-applying rollers. The elements are maintained in superposed relation for a predetermined period, preferably for a duration of 15 to 120 seconds, during which exposed silver halide is reduced to silver and unreduced silver halide forms a water-soluble, complex salt which diffuses through the layer of solution to the image-receiving element, there to be reduced to an argental image. At the end of this period, the silver halide element is separated from the image-receiving element. Materials useful in such a transfer process are well known in the art.

The photosensitive element may be any of those conventionally used in silver diffusion transfer processes and generally comprises a silver halide emulsion carried on a base, e.g., glass, paper or plastic film. The silver halide may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers.

The image-receiving element preferably includes certain materials, the presence of which, during the transfer process has a desirable effect on the amount and character of silver precipitated on the image-receiving element. Materials of this type are known in the art.

Separating of the silver halide element from the image-receiving element may be controlled so that the layer of processing composition is removed from the image-receiving element or the layer of the processing composition is caused to remain in contact with the image-receiving element, e.g., to provide it with a protective coating. Techniques which enable such results to be accomplished as desired are described in U.S. Pat. No. 2,647,054. In general, the processing reagents are selected so that traces remaining after the solidified processing layer has been separated from the silver image or which remain in said layer adhered as a protective coating on the silver image, as indicated above, are colorless or pale, so as not to appreciably affect the appearance of the image and to have little or no tendency to adversely react with the silver image.

The silver halide solvents of the present invention also may be employed in diffusion transfer processes adapted to provide positive silver transfer images which may be viewed as positive transparencies without being separated from the developed negative silver image including such processes adapted for use in forming additive color projection positive images. Diffusion transfer processes of this type are known in the art. See, for example, U.S. Pat. Nos. 3,536,488, 3,615,428, and 3,894,871. The subject compounds also find utility in silver halide solvents in diffusion transfer processes utilizing the properties of the imagewise distribution of silver ions in the soluble silver complex made available in the undeveloped and partially developed areas of a silver halide emulsion to liberate a reagent, e.g., a dye in an imagewise fashion, as described in U.S. Pat. No. 3,719,489.

As noted above, in diffusion transfer film units the negative component comprising at least one photosensitive layer and the positive component comprising an image-receiving layer may be in separate sheet-like elements which are brought together during processing and thereafter either retained together as the final print or separated following image formation.

Rather than the photosensitive layer and the image-receiving layer being in separate elements, they may be in the same element. In one such film unit, the image-receiving layer is coated on a support and the photosensitive layer is coated on the upper surface of the image-receiving layer. The liquid processing composition is applied between the combined negative-positive element and a second sheet-like element or spreading sheet which assists in spreading the liquid composition in a uniform layer adjacent to the surface of the photosensitive layer.

Still other film units are those where the negative and positive components together may comprise a unitary structure wherein the image-receiving layer carrying the transfer image is not separated from the developed photosensitive layer(s) after processing but both components are retained together as a permanent laminate. Such film units include those for providing positive silver transfer images which may be viewed as positive color transparencies, such as, those described in U.S. Pat. No. 3,894,871. Other integral film units also include those adapted for forming a transfer image, in color or in black and white, viewable by reflected rather than by transmitted light. In addition to the aforementioned photosensitive layer(s) and image-receiving layer, such film units include means for providing a reflecting layer between the image-receiving and photosensitive layer(s) in order to mask the developed photosensitive layer(s) and to provide a white background for viewing the transfer image. This reflecting layer may comprise a preformed layer of a reflecting agent included in the film unit or the reflecting agent may be provided subsequent to photoexposure, for example, by including the reflecting agent in the processing composition. In addition to these layers, the laminate usually includes dimensionally stable outer layers or supports, at least one of which is transparent so that the resulting transfer image may be viewed by reflection against the background provided by the light-reflecting layer. Integral negative-positive film units wherein the photosensitive and image-receiving layers are retained as a permanent laminate after processing are described, for example, in U.S. Pat. Nos. 3,415,644; 3,647,437 and 3,594,165.

It will be appreciated that in the formation of color transfer images, a dye image-providing material such as the compounds of U.S. Pat. No. 3,719,489 may be associated with the photosensitive silver halide layer or layers of the negative component.

The diffusion transfer film units described above are employed in conjunction with means, such as, a rupturable container containing the requisite processing composition and adapted upon application of pressure of applying its contents to develop the imagewise exposed film unit.

To illustrate the utility of the above-described compounds as photographic silver halide complexing agents, certain of the compounds were incorporated in photographic processing composition which were then employed in a photographic method. In one such illustrative showing a film unit was prepared comprising a transparent polyester film base carrying on one surface an additive color screen of approximately 1000 triplets per inch of red, blue and green filter screen elements in repetitive side by side relationship; an approximately 4 micron thick polyvinylidene chloride barrier layer; a nucleating layer comprising 0.23 mg/ft$^2$ of palladium nuclei (as metal), 0.29 mg/ft$^2$ of gelatin, 0.35 mg/ft$^2$ of tin (as metal) and 0.47 mg/ft$^2$ of total chloride (associated with Pd and Sn); an interlayer of 2.21 mgs/ft$^2$ of deacetylated chitin, 0.645 mg/ft$^2$ of copper acetate (dihydrate), 0.178 mg/ft$^2$ of sodium acetate and 0.194 mg/ft$^2$ of alkyl phenoxy polyoxy ethylene glycol; a hardened gelatino silver iodobromo emulsion coated at a coverage of about 85 mgs/ft$^2$ of silver, 114 mgs/ft$^2$ of gelatin, 50 mgs/ft$^2$ of Dow 620 carboxylated styrene butadiene latex, 4.56 mgs/ft$^2$ of propylene glycol alginate and 0.55 mg/ft$^2$ of chrome alum (coverage as $K_2Cr(SO_4)_2 \cdot 12H_2O$); and an antihalo top coat of 300 mgs/ft$^2$ of gelatin, 175 mgs/ft$^2$ of Dow 620 carboxylated styrene butadiene latex, 8.8 mgs/ft$^2$ of propylene glycol alginate, 1.2 mgs/ft$^2$ of dioctyl ester of sodium succinic acid, 5.6 mgs/ft$^2$ of pyridinium bis-1,5(1,3-diethyl-2-thiol-5-barbituric acid) pentamethine oxanol, 7.0 mgs/ft$^2$ of 4-(2-chloro-4-dimethylamino benzaldehyde)-1-(p-phenyl carboxylic acid)-3-methyl pyrazolone-5 and 5.0 mgs/ft$^2$ of benzimidazole-2-thiol gold $Au^{+1}$ complex (as gold).

A film unit as identified above was exposed through the additive color screen to a step wedge. After a polyester cover sheet was superposed over the film unit it was processed, while being retained intact, by spreading a layer of processing composition less than about 1.2 mils thick between the antihalo top coat layer and the cover sheet. The processing composition was prepared by adding 0.4 ml of compound A to 10 ml of the following formulation:

| | |
|---|---|
| Water | 79.02 g. |
| Hydroxyethyl cellulose | 0.84 g. |
| Sodium hydroxide | 10.04 g. |
| Tetramethyl reductic acid | 8.38 g. |
| Sodium sulfite | 0.97 g. |
| Potassium bromide | 0.73 g. |
| 4-aminopyrazolo (3,4-d) pyrimidine | 0.019 g. |

After an imbibition period of about one minute the cover sheet was stripped away and the maximum and minimum densities of the resultant image were determined with a transmission densitometer. The values were as follows:

| | Red | Green | Blue |
|---|---|---|---|
| D Max | 1.83 | 2.31 | 3.33 |
| D Min | 0.80 | 0.98 | 1.45 |

In another illustrative showing, a film unit was prepared as follows: the light sensitive element comprised a transparent polyester film base carrying on one surface an additive color screen of approximately 1500 triplets per inch of red, blue and green filter screen elements in repetitive side by side relationship; a composite barrier structure made up of an approximately 0.7 micron thick layer of polyvinylidene chloride coated from a solvent, an approximately 1.0 micron thick layer of polyvinylidene chloride coated from water emulsion and an approximately 0.3 micron thick layer of polyvinyl formal; a nucleating layer as described in the previous example; an interlayer of 1.94 mgs/ft$^2$ of gelatin, and 0.194 mg/ft$^2$ of alkyl phenoxy polyoxy ethylene glycol; a hardened gelatino silver iodobromo emulsion coated at a coverage of about 85 mgs/ft$^2$ of silver, 85 mgs/ft$^2$ of gelatin, 7.5 mgs/ft$^2$ of propylene glycol alginate, 0.41 mg/ft$^2$ of chrome alum (coverage as $K_2Cr(SO_4)_2$, and 0.61 mg/ft$^2$ of alkyl phenol polyglycol ether (average 9.5 mols ethylene oxide) surfactant; and an antihalo top coat as described in the film unit of the previous example with the exception that 22 mgs/ft$^2$ of propylene glycol alginate were present.

The cover sheet comprised a 4 mil thick polyester support having a thin coating on one surface to prepare the support for coating. Coated on the support in the following order were:

(A) An acid providing layer formed by combining 60 parts by volume of a 30% solution of the half butyl ester of ethylene maleic anhydride in methyl ethyl ketone and 40 parts by volume of a solution of 5.7% Butvar B-72 (available from Monsanto), 63.3% ethyl acetate and 31% n-butanol and coating the mixture on the support to provide a dry coverage of about 2.45 mgs/ft$^2$; and (B) A gelatin layer formed by coating a water solution containing 10% deionized gelatin, and 0.05% Emulphor ON-870 (available from Antara Chemical Co.) to provide a dry coverage of about 1 mg/ft$^2$.

The film unit as identified above was exposed through the additive color screen to a step wedge and processed while being retained intact, by spreading a layer of a processing composition less than about 3 mils thick between the cover sheet and the light sensitive element. The processing composition was prepared by adding 0.5 ml of compound (B) to 10 ml of the following formulation:

| | |
|---|---|
| Water | 82.36 g. |
| Sodium hydroxide | 7.265 g. |
| Hydroxyethyl cellulose | 2.811 g. |
| Sodium sulfite | 2.54 g. |
| Tetramethyl reductic acid | 3.17 g. |
| Dodecyl-N,N-dipyridinium dibromide | 1.78 g. |
| 4-aminopyrazolo (3,4-d) pyrimidine | 0.016 g. |
| 5-bromo-6-methyl-4-azabenzimidazole | 0.016 g. |
| Thiazololidine-2-thione | 0.035 g. |

After an imbibition period of about one minute the maximum and minimum densities of the image were determined on a transmission densitometer. The values were as follows:

| | Red | Green | Blue |
|---|---|---|---|
| D Max | 1.58 | 1.69 | 1.64 |
| D Min | 0.29 | 0.31 | 0.38 |

When examined visually 17 days after processing no crystals were apparent in the transparency. The image was stored under ambient conditions during the interim.

It will be apparent that the relative proportions of the subject silver halide solvents and of the other ingredients of the processing compositions may be varied to suit the requirements of a given photographic system. Also, it is within the scope of this invention to modify the formulations set forth above by the substitution of alkalies, antifoggants and so forth other than those specifically mentioned. Where desirable, it is also contemplated to include in the processing compositions, other components as commonly used in the photographic art.

The invention will now be described further in detail with respect to specific preferred embodiments by way of examples, it being understood that these are illustrative only and the invention is not intended to be limited to the materials, conditions, process parameters, etc., recited therein. All parts and percentages are by weight unless otherwise indicated.

EXAMPLES

Preparation of N,N'-dimethyl-N,N'-bis(2-mercaptoethyl)-ethylene diamine

A 250 ml three-neck flask, equipped with a magnetic stirrer, addition funnel, thermometer and argon inlet was charged with a solution of 18.3 g. (0.208 mol) of N,N'-methylethylenediamine in 70 ml of benzene. A solution of 25.1 g. (0.417 mol) of ethylene sulfide in 10 ml of benzene was added with stirring to the solution in the flask under argon while maintaining the temperature of the solution in the flask at 50°-55° C. The resulting clear solution was allowed to remain overnight at ambient temperature, washed with two 5 ml portions of water and dried over magnesium sulfate. The solvent was removed under reduced pressure and 39.9 g. (97% yield) of a colorless oil was obtained.

The material is susceptible to air oxidation and therefore further purification was not carried out. The material can be stored up to a week under argon in a freezer without any significant deterioration. Since the compound has an extremely unpleasant odor and can cause severe skin allergy careful handling is necessary.

EXAMPLE I

Preparation of Compound B

A three neck liter flask equipped with an overhead stirrer, addition funnel and argon inlet, and an oil bath was charged with 14.5 g. of a 50% sodium hydride dispersion in oil (0.26 molar in NaH). Most of the oil was removed by repeated washings with petroleum ether carried out under argon. In each washing about 15–20 ml of petroleum ether were added to the dispersion, the dispersion stirred briefly and allowed to settle and supernatant liquid removed with a syringe. 520 ml of spectrograde dimethylformamide were then introduced into the dispersion and the reaction flask was heated with the oil bath maintained at about 95° C. When the internal temperature of the flask reached about 75° C. there was begun the dropwise addition, with vigorous stirring, of a mixture of 27.08 g. (0.13 mole) of N,N'-dimethyl-N,N'-bis(2-mercaptoethyl)ethylenediamine and 18.6 g. (0.13 mole) of bis-2-chloroethylether in 40 ml dimethylformamide. Addition of the mixture was completed in about 2½ hours. The temperature was maintained at about 80°-85° C. throughout the addition of the mixture and for about 16 hours thereafter. Most of the solvent was removed in vacuo with the bath temperature at about 70°-75° C. The resulting thick light brown oil was dissolved in 300 ml of ethylacetate, washed with three 20 ml portions of water and dried over magnesium sulfate. Removal of the solvent under reduced pressure gave 34 g. of a light brown syrup. $^{13}C$ NMR and chromatographic analysis showed this to be a complex mixture of products.

A solution of 18 g. of the crude product in 200 ml of methanol was formed and to it there were added 10.9 g. of silver thiocyanate in portions. Toward the end of the silver thiocyanate addition dissolution of the silver salt became slow and a sticky material separated from solution. The mixture was stirred for about 15 minutes after which the soluble portion was removed, diluted with 100 ml of methanol and filtered through Celite 542 (a diatomaceous earth material available from Johns Manville Co.). The filtrate was concentrated to 120 ml under reduced pressure and stored for two days in a refrigerator. Light yellow crystals deposited during storage and these were collected, washed with methanol and recrystallized from methanol twice at low temperature by first dissolving the crystals in excess solvent at 40° C. and then concentrating to about one-half the initial volume. The crystals were then dried under high vacuum. A total of 8.5 g. of 1:1 compound B-silver thiocyanate complex, m.p. 147°-149° C. was recovered. Recrystallization of a small sample of this material gave essentially colorless crystals, m.p. 149°-150° C. $C_{13}H_{26}N_3OS.Ag$ requires 35.13%C, 5.896%H, 9.46%N, 21.64%S and 24.27%Ag. Elemental analysis of this material gave 35.03%C, 5.91%H, 9.50%N, 21.60%S and 24.43%Ag. Also NMR spectral data were consistent with a compound B-silver thiocyanate complex.

8.3 g. (18.7 moles) of the complex were dissolved in 100 ml of a 70:30 (vol/vol) mixture of dichloromethane and ether and treated with hydrogen sulfide gas to precipitate silver as silver sulfide. Bubbling of hydrogen sulfide was continued until an aliquot of the supernatant solution gave no precipate with hydrogen sulfide. The mixture was then stirred for about 15 minutes, filtered through Celite 542 and the filtrate was concentrated to a thick colorless syrup, presumably a thiocyanic acid complex of ligand B. The free ligand, compound B, was obtained from this material by the following alternative procedures:

(A) A column of a strongly basic, quaternary ammonium (polystyrene) type, anion exchange resin (Amberlite IRA-400) was prepared in carbonate-free water, washed with dilute sodium hydroxide and then thoroughly with water until the eluent was not basic. An aqueous solution of the above colorless syrup was passed through the column and washing with carbonate-free water was continued until most of the material had been eluted. The combined washings were concentrated under reduced pressure. The residual syrup was dissolved in absolute ethanol, filtered through Celite 542 and the filtrate concentrated to provide about 5 g. of compound B as a clear colorless syrup. The sample was dried at 50° C. by pumping under high vacuum.

(B) Alternatively, the aqueous solution of the bisthiocyanic acid complex was treated with a stoichiometric amount of a 10% aqueous tetramethylammonium hydroxide solution and extracted with ethylacetate or dichloramethane. The organic layer was washed with water and dried over anhydrous sodium sulfate. Removal of the solvent gave compound B as a colorless syrup.

$C_{12}H_{26}N_2S_2O$ requires 51.75%C, 9.41%H, 10.06%N, 23.03%S and 5.74%O. Elemental analysis gave 51.74%C, 9.39%H, 10.02%N and 22.84%S.

EXAMPLE II

Preparation of Compounds C & D

A solution of 0.25 g. of compound A in 5 ml of tetrahydrofuran was formed, cooled in an ice bath and to it was added dropwise over a period of about 15 minutes a solution of 0.186 g. of p-nitrobenzoyl chloride in 5 ml tetrahydrofuran. The solution was stored overnight in a refrigerator, warmed to 0° C. and then stirred at room temperature for about four hours. The solvent was removed and the residue triturated with ice. A semi-solid was obtained and extracted with dichloromethane. The extract was washed with dilute sodium hydroxide until the aqueous layer was slightly basic and then dried over sodium sulfate. Examination of the product by thin layer chromatography on silica gel using a 20:1 (vol/vol) ethylacetate-ethanol mixture as the eluent showed the product to be a mixture of the mono-(compound C) and diacylation (compound D) product as well as starting material.

The diacylation product, m.p. 196°-197° C. was separated by recrystallization from absolute ethanol. The filtrate, upon removing the diacylation product, was concentrated. Examination of the concentrate by thin layer chromatography on silica gel using a 85:15 (vol/vol) benzene-methanol mixture showed it to contain primarily the monoacylation product (compound C) and the starting material along with minor impurities. The monoacylation product was isolated as a thick syrup by chromatographing the product two additional times under the same conditions. The NMR spectrum of the product was consistent with compound C.

EXAMPLE III

Preparation of Compound D

A suspension of 0.322 g. of the dihydrochloride salt of compound A in 5 ml of benzene was treated with 2 ml of dimethylformamide to dissolve most of the solid, followed by the addition of 0.28 ml triethylamine. Then a solution of 0.186 g. of p-nitrobenzoyl chloride in 2 ml tetrahydrofuran was added dropwise and the mixture stirred overnight at room temperature. The mixture was concentrated, diluted with 15 ml of ice water, extracted with three 15 ml portions of dichloromethane and dried over magnesium sulfate. The product was concentrated to give a thick syrup which solidified when triturated with methanol at ice bath temperature. The solid was filtered, washed with methanol and dried under reduced pressure to give a white solid, m.p. 195°-198° C. The NMR spectrum was consistent with compound D.

EXAMPLE IV

Preparation of Compounds E & F

A solution of 0.38 g. of compound A in 10 ml dry ether was formed and cooled in an ice bath. The solution was treated with ethereal hydrochloric acid (HCl gas dissolved in ether at 0° C.) until the supernatant liquid showed no turbidity upon additional treatment with ethereal hydrochloric acid. A white solid (the dihydrochloride salt of compound A) separated from solution, was removed by filtration and washed with ether.

To a stirred suspension of 0.32 g. of the dihydrochloride salt of compound A in 2 ml of 6% potassium hydroxide solution there was added 0.23 g. of tosyl chloride. The mixture was warmed to a temperature of 50°-60° C. for about 15 minutes and then cooled in an ice bath. The solid which formed was removed by filtration, washed with water and crystallized from ethanol to provide colorless, needle-like crystals, m.p. 170°-172° C. The NMR spectrum of the material was consistent with the ditosylate (compound F).

After removing the ditosylate the aqueous filtrate was extracted with dichloromethane and the extract dried and concentrated. The material was then chromatographed on silica gel using an 80:20 mixture of ethylacetate-ethanol as the eluent to separate the monotosylate (compound E) as a colorless syrup which solidified on standing at room temperature, m.p. 71°-73° C. The NMR spectrum of the material was consistent with the monotosylate.

EXAMPLE V

Preparation of Compounds G & H 125 mg of compound A were dissolved in 1.5 ml of dichloromethane and to the solution were added dropwise, with stirring, 0.05 ml of acetic anhydride. The mixture was heated under reflux for 6 hours and then stirred overnight at room temperature. The solvent was removed and the residue taken up in 25 ml of dichloromethane, washed sequentially with 0.5 N hydrochloric acid, 3% sodium bicarbonate and water. The extract was dried over magnesium sulfate and concentrated under reduced pressure to give the crude product mixture as a semi-solid. Crystallization from absolute ethanol gave colorless crystals, m.p. 145°–146° C. The NMR spectrum was consistent with compound G.

EXAMPLE VI

Preparation of Compound I

To a suspension of 0.24 g. of a 50% sodium hydride dispersion in oil (which had previously been washed free of oil with petroleum ether) in 15 ml of dimethylformamide was added 0.95 g. of mechlorethamine hydrochloride. To the resulting free amine were added 1.05 g. of N,N'-dimethyl-N,N'-bis(2-mercaptoethyl) ethylenediamine in 5 ml of dimethylformamide.

To a separate three neck flask there was added 0.5 g. of a 50% sodium hydride dispersion in oil and this was washed free of oil with petroleum ether under argon. To this were added 50 ml of dimethylformamide and the suspension was heated to 80°–90° C. The mixture of the two reactants prepared above was then added dropwise with vigorous stirring over a period of about 25 minutes and stirring was continued at that temperature overnight. The solvent was then removed under reduced pressure, the residue taken up in 25 ml of ethyl acetate, washed twice with two 5 ml portions of water and dried over sodium sulfate. Removal of the solvent gave 1.4 g of a slightly colored syrup. $^{13}$C NMR and thin layer chromatographic analysis on silica gel using a 50:50 (vol/vol) mixture of ethylacetate-hexane showed this to be a mixture of products. Purification by column chromatography on silica gel gave 0.5 g of compound I which was characterized by $^{13}$C NMR and mass spectrum (m/e=291, parent ion and 292 P+1).

A stirred solution of 116 mg of compound I in 5 ml methanol was treated with 66.4 mg of silver thiocyanate. After 10 minutes the mixture was filtered to remove traces of suspended material and the solvent removed under reduced pressure to give a white crystalline solid, m.p. 160°–162° C. The product was crystallized from methanol by storing for several days in a refrigerator. Needle-like crystals formed and these were collected by filtration and washed to give colorless needles, m.p. 164°–165° C.

$C_{14}H_{29}N_4S_3$ AG requires 36.75%C, 6.39%H, 12.25%N, 21.03%S and 23.58%AG. Elemental analysis of the product gave 36.70%C, 6.35%H, 12.29%N, 21.03%S and 23.74%AG.

EXAMPLE VII

Preparation of Compound J

In a two-neck flask 0.24 g. of a 50% sodium hydride dispersion in oil was washed free of oil with petroleum ether under argon atmosphere and then 15 ml of dimethylformamide were introduced with a syringe. The suspension was stirred for 5 minutes and 0.89 g. of bischloroethylamine hydrochloride was added with stirring followed by the addition of 1.5 g. of N,N'-dimethyl-N-N'-bis(2-mercaptoethyl) ethylenediamine.

In a separate 3-neck flask equipped with an addition funnel there was added 0.5 g. of a 50% sodium hydride dispersion in oil which was then washed free of oil with petroleum ether under argon. Then 45 ml of dimethylformamide were added and the suspension was stirred at a temperature of 80°–90° C. To the suspension was added dropwise over a period of 1.5 hours the reactant mixture described above. Stirring was continued overnight at that temperature and then for an additional period at room temperature. Most of the solvent was removed under reduced pressure and the residue was taken up in 30 ml ethyl acetate, washed twice with 5 ml portions of water and dried over sodium sulfate. Removal of the solvent gave a clear light brown syrup.

The product was purified by column chromatography on silica gel using an ethyl acetate-ethanol mixture for elution. NMR spectra of the product were consistent with compound J.

EXAMPLE VIII

Preparation of Compound K

To a solution of 138 mg of compound J in 10 ml dichloromethane there was added dropwise, with stirring under argon at 5°–10° C., a solution of 120 mg of p-nitrophenylchloroformate in 2 ml dichloromethane. Stirring was continued overnight at room temperature after which it was diluted with 10 ml of dichloromethane, washed with dilute sodium carbonate solution, then with water and dried over magnesium sulfate. Evaporation of the solvent under reduced pressure gave a light yellow syrup which solidified on standing.

The solid was chromatographed on a silica gel plate using a 90:10 (vol/vol) ethyl acetate-ethanol mixture. The major band was removed and eluted with methanol. Removal of the solvent gave a solid which was then dissolved in ether, filtered through Celite 542, the filtrate concentrated and the last traces of ether removed under reduced pressure. A pale solid m.p. 103°–107° C. was obtained. This solid was recrystallized twice from methanol to give a pale yellow crystalline solid m.p. 109°–110° C., which was dried under reduced pressure.

$C_{19}H_{30}N_4O_4S_2$ requires 51.56%C, 6.83%H, 12.66%N, 14.49%S and 14.46%O. Elemental analysis of the product gave 51.63%C, 6.62%H, 12.56%N and 14.39%S.

EXAMPLE IX

Preparation of Compound L

In a 250 ml three neck flask equipped with an addition funnel, reflux condenser and a serum cap there were added 1.01 g. of 50% sodium hydride dispersion in oil. The dispersion was washed free of oil by repeated treatments of petroleum ether under argon. Most of the petroleum ether was removed with a syringe and the last traces removed by blowing with argon. Dimethylformamide (70 ml) was added and the suspension heated to 70°–80° C. To the stirred suspension there was slowly added dropwise over a period of 2 hours at a temperature of 85°–90° C., a mixture of 2.1 g. of N,N'-dimethyl-N,N'-bis(2-mercaptoethyl) ethylenediamine and 1.58 g. of bis-2-chloroethylsulfide in 15 ml dimethylformamide. Stirring was continued overnight at 85°–90° C. after which the solvent was removed under reduced pressure. The residue was extracted with ethyl acetate, washed three times with 5 ml portions of water and dried over magnesium sulfate. The residue was concentrated to give a brown syrup and the last traces of solvent removed under reduced pressure. The product was purified by chromatography with silica gel using ethyl acetate as the eluent to furnish compound L as a pale-colored syrup which solidified under refrigeration.

$C_{12}H_{26}N_2S_3$ requires 48.93%C, 8.89%H, 9.51%N and 32.66%S. Elemental analysis of the product gave 48.88%C, 8.80%H, 9.38%N and 32.51%S.

Although the invention has been described with respect to various preferred embodiments thereof, it is not intended to be limited thereto but rather those skilled in the art will recognize that modifications and variations

What is claimed is:

1. A compound represented by the formula

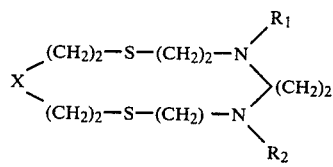

wherein X is selected from the group consisting of oxygen, sulfur and —NR₃;

R₁ and R₂ are the same or different and are H, alkyl, hydroxyalkyl, alkoxyalkyl,

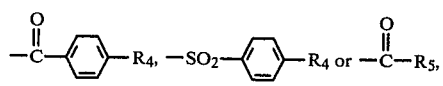

provided that both R₁ and R₂ are not H, wherein R₄ is H, alkyl, alkoxy or —NO₂ and R₅ is H, alkyl, alkoxy or alkoxyalkyl; and R₃ is H, alkyl, hydroxyalkyl, alkoxyalkyl,

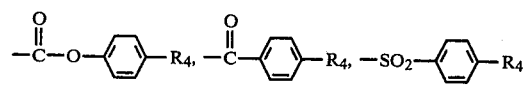

or —CH₂—CH=CH—R₆, wherein R₆ is H, alkyl, cyano or

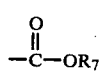

wherein R₇ is H or alkyl.

2. A compound as defined in claim 1 wherein R₁, R₂ and R₃ are independently selected from the group consisting of alkyl, hydroxyalkyl, and alkoxyalkyl having from two to six carbon atoms.

3. A compound as defined in claim 1 which is represented by the formula

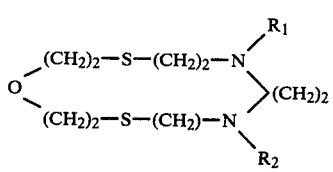

wherein R₁ and R₂ are the same or different and are H, alkyl, hydroxyalkyl, alkoxyalkyl,

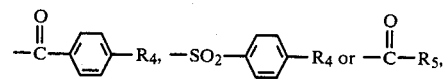

wherein R₄ is H, alkyl, alkoxy or —NO₂ and R₅ is H, alkyl, alkoxy or alkoxyalkyl, provided that both R₁ and R₂ are not H.

4. A compound as defined in claim 3 wherein R₁ and R₂ are independently selected from the group consisting of alkyl, hydroxyalkyl, and alkoxyalkyl having from two to six carbon atoms.

5. A compound as defined in claim 1 which is represented by the formula

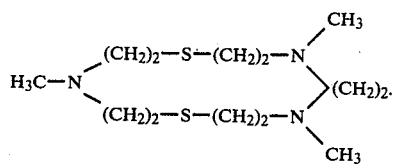

6. A compound as defined in claim 1 which is represented by the formula

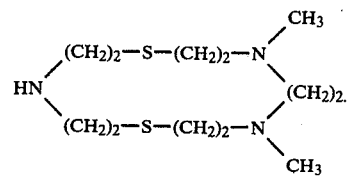

7. A compound as defined in claim 1 which is represented by the formula

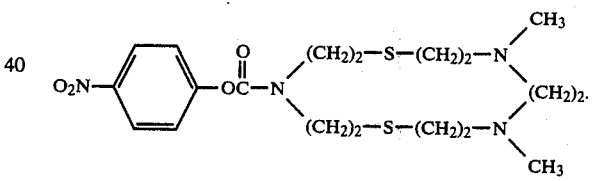

8. A compound as defined in claim 1 which is represented by the formula

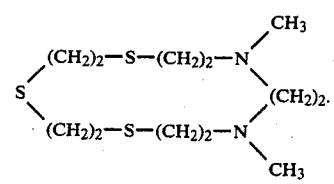

9. A compound as defined in claim 1 wherein X is sulfur or —NR₃.

* * * * *